US008524972B1

(12) United States Patent
Weber et al.

(10) Patent No.: US 8,524,972 B1
(45) Date of Patent: Sep. 3, 2013

(54) LOW TEMPERATURE STEAM STRIPPING FOR BYPRODUCT POLYMER AND SOLVENT RECOVERY FROM AN ETHYLENE OLIGOMERIZATION PROCESS

(75) Inventors: Michael W. Weber, Houston, TX (US); Randy L. Foster, Crosby, TX (US); James R. Lattner, Laporte, TX (US); Jimmy L. Tardy, Crosby, TX (US); Michael J. Veraa, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 2 days.

(21) Appl. No.: 13/449,839

(22) Filed: Apr. 18, 2012

(51) Int. Cl.
*C07C 7/00* (2006.01)
*B01D 3/38* (2006.01)

(52) U.S. Cl.
USPC ........... 585/809; 585/802; 208/255; 208/356; 208/362

(58) Field of Classification Search
None
See application file for complete search history.

(56) References Cited

U.S. PATENT DOCUMENTS

| | | | |
|---|---|---|---|
| 3,300,458 A | 1/1967 | Manyik et al. |
| 4,472,525 A | 9/1984 | Singleton |
| 4,689,437 A | 8/1987 | Murray |
| 4,777,315 A | 10/1988 | Levine et al. |
| 5,376,612 A | 12/1994 | Reagen et al. |
| 5,451,645 A | 9/1995 | Reagen et al. |
| 5,557,026 A | 9/1996 | Tanaka et al. |
| 5,563,312 A | 10/1996 | Knudsen et al. |
| 5,668,249 A | 9/1997 | Baardman et al. |
| 5,689,028 A | 11/1997 | Lashier et al. |
| 5,731,487 A | 3/1998 | Tamura et al. |
| 5,763,723 A | 6/1998 | Reagen et al. |
| 5,814,575 A | 9/1998 | Reagen et al. |
| 5,853,551 A | 12/1998 | Boucot et al. |
| 5,856,610 A | 1/1999 | Tamura et al. |
| 5,859,303 A | 1/1999 | Lashier |
| 5,919,996 A | 7/1999 | Freeman et al. |
| 5,968,866 A | 10/1999 | Wu |
| 6,031,145 A | 2/2000 | Commereuc et al. |
| 6,265,513 B1 | 7/2001 | Murray et al. |
| 6,268,447 B1 | 7/2001 | Murray et al. |
| 6,277,841 B1 | 8/2001 | Rajagopalan et al. |
| 6,303,719 B1 | 10/2001 | Murray et al. |
| 6,320,002 B1 | 11/2001 | Murray et al. |
| 6,337,297 B1 | 1/2002 | Mimura et al. |
| 6,380,451 B1 | 4/2002 | Kreischer et al. |
| 6,455,648 B1 | 9/2002 | Freeman et al. |
| 6,521,806 B1 | 2/2003 | Tamura et al. |
| 6,583,083 B2 | 6/2003 | Murray et al. |
| 6,800,702 B2 | 10/2004 | Wass |
| 7,157,612 B2 | 1/2007 | Ewert et al. |

(Continued)

FOREIGN PATENT DOCUMENTS

WO 2005/084772 9/2005
WO 2007/092136 8/2007

(Continued)

*Primary Examiner* — Tam M Nguyen
(74) *Attorney, Agent, or Firm* — Robert L. Abdon

(57) ABSTRACT

This disclosure relates generally to low temperature steam stripping methods for byproduct polymer and solvent separation from an ethylene oligomerization process. The methods disclosed have been found to separate byproduct polymer from solvent without fouling process equipment or causing other process problems. The byproduct polymer ends up as flowable solid particles in a water stream that may be easily discharged from the process, while solvent is recovered for recycle to the process. In embodiments of the invention, over 90 wt % of the solvent used is recovered and the discharged byproduct polymer is less than 20 wt % solvent.

21 Claims, 1 Drawing Sheet

(56) References Cited

U.S. PATENT DOCUMENTS

| | | |
|---|---|---|
| 7,414,006 B2 | 8/2008 | McConville et al. |
| 7,425,661 B2 | 9/2008 | McConville et al. |
| 7,638,670 B2 | 12/2009 | McConville et al. |
| 7,638,671 B2 | 12/2009 | McConville et al. |
| 7,687,672 B2 | 3/2010 | Buchanan et al. |
| 7,858,833 B2 | 12/2010 | Buchanan et al. |
| 8,067,609 B2 | 11/2011 | Ackerman et al. |
| 8,076,524 B2 | 12/2011 | Lattner et al. |
| 8,138,348 B2 | 3/2012 | Ackerman et al. |
| 8,212,047 B2 | 7/2012 | Hagadorn et al. |
| 8,227,653 B2 | 7/2012 | Weber et al. |
| 2008/0058486 A1 | 3/2008 | McCullough et al. |
| 2008/0188633 A1 | 8/2008 | Ackerman et al. |
| 2008/0200743 A1 | 8/2008 | Ackerman et al. |
| 2012/0238713 A1 | 9/2012 | Hagadorn et al. |

FOREIGN PATENT DOCUMENTS

| | | |
|---|---|---|
| WO | 2007/092217 | 8/2007 |
| WO | 2009/060343 | 5/2009 |
| WO | 2011/112184 | 9/2011 |

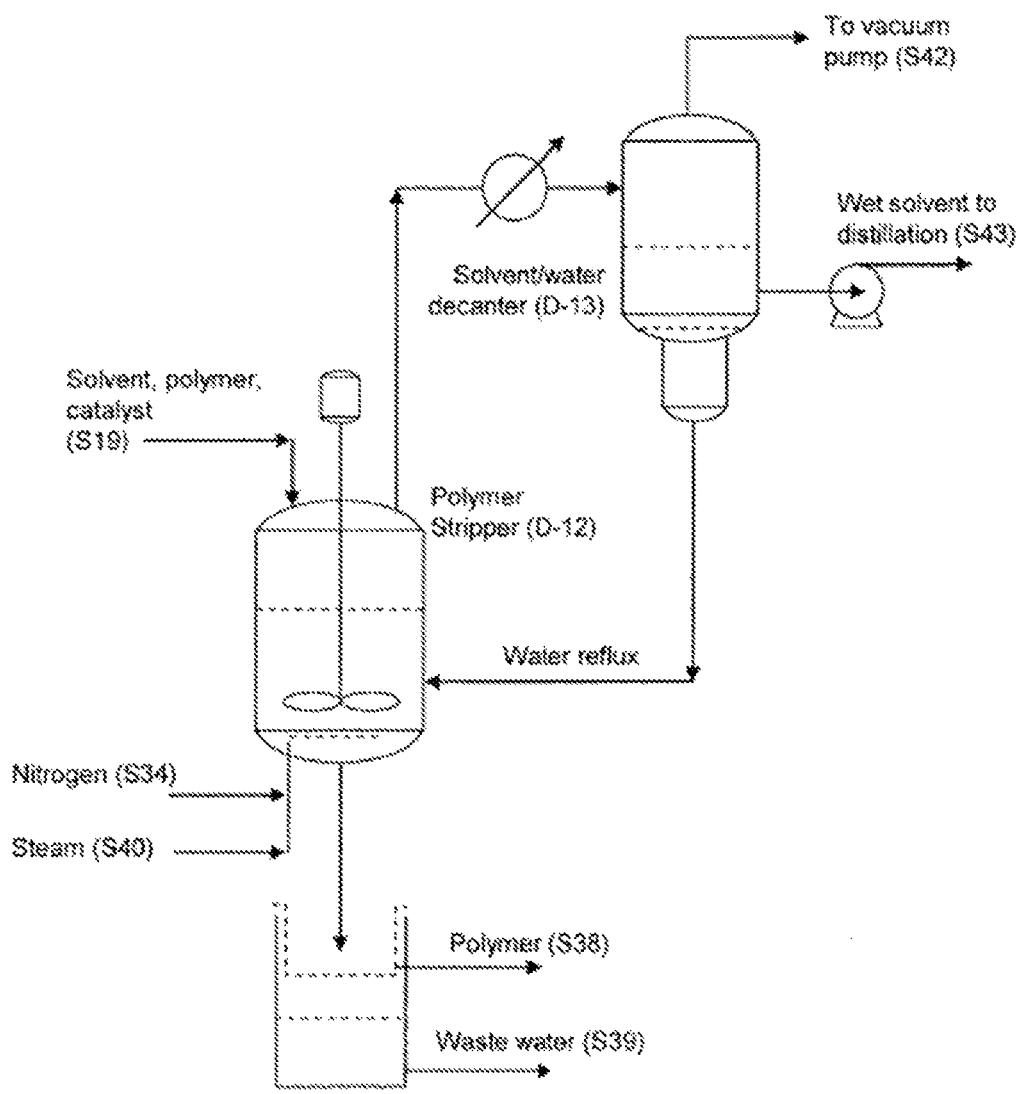

LOW TEMPERATURE STEAM STRIPPING FOR BYPRODUCT POLYMER AND SOLVENT RECOVERY FROM AN ETHYLENE OLIGOMERIZATION PROCESS

FIELD

This disclosure relates generally to low temperature steam stripping methods for byproduct polymer and solvent recovery from an ethylene oligomerization process.

BACKGROUND

Ethylene oligomerization can produce 1-hexene at high selectivity using homogeneous, single-site chromium catalyst systems, activated by a molar excess of alkyl aluminums such as methyl alumoxane (MAO) and modified methyl alumoxane (MMAO). The trimerization of ethylene to 1-hexene represents one method of manufacturing desired oligomer products. Similarly, 1-octene and other desired oligomer products can be produced in high selectivity via ethylene oligomerization using homogeneous chromium catalyst systems activated by an appropriate aluminum compound. Such selective oligomerization reactions have been performed for many years with numerous optimization efforts. Exemplary processes of the reaction chemistry include U.S. Pat. No. 7,157,612 and International Patent Publications WO 2007/092136 and WO 2009/060343.

A major challenge associated with the selective oligomerization of ethylene is control of the reaction to maximize production rates while maintaining selectivity to the desired oligomers and maximizing catalyst utilization rates. Many ethylene oligomerization processes produce unwanted byproduct polymer which can foul process equipment and cause other process problems. For example, in an unavoidable side reaction, a small fraction of the converted ethylene forms polyethylene. This polyethylene can take any or all of the following three forms: (1) coat surfaces of the reactor and associated piping; (2) flow out of the reactor in solution with the reaction mixture; or (3) flow out of the reactor as a suspended solid in the reaction mixture. In addition, the formation of this byproduct polymer can continue downstream of the reaction system due to the presence of the still-active homogeneous catalyst in the reactor effluent.

A number of procedures have been developed for dealing with the problems of byproduct polymer formation and the presence of active catalyst in the reactor effluent in ethylene trimerization processes. For example, U.S. Pat. No. 6,380,451 discloses a method for killing the catalyst after it leaves an ethylene trimerization reactor by contacting the reactor effluent with an alcohol. An excess of alcohol is required, with a 5:1 mole ratio of alcohol to total catalyst metals being preferred. The preferred alcohol is one with a high enough boiling point that it can be easily separated from the desired hexene product by distillation. This patent also discloses a method for cleaning the polymer and catalyst residues that deposit on the internal surfaces of the reactor. The polymer is removed by periodic washing with the reaction diluent at a temperature 60° C. to 70° C. higher than the trimerization reaction temperature. In addition, this patent discloses cyclohexane as the preferred diluent/solvent in the reactor, as a good solvent is preferred to keep the catalyst system in solution.

U.S. Pat. No. 7,157,612 discloses another method for recovering byproduct polymer. Precipitation of byproduct polymer within the reactor is minimized by operating the reactor temperature high enough to keep the polymer in solution, with a preferred temperature of at least 110° C. On leaving the reactor, the effluent is contacted with an alcohol to deactivate the catalyst system. The effluent can then either be cooled, in which case some of the byproduct polymer precipitates and can be separated by filtration, or kept hot so that polymer stays in solution. In either case, soluble byproduct polymer continues to the downstream distillation columns where it is distilled away from the reaction products, diluents, and alcohol. In this manner, the byproduct polymer ends up with the catalyst and heavy byproduct residues.

Some other trimerization catalyst systems have been developed which permit the ethylene trimerization reaction to be carried out with high selectivity. For example, U.S. Pat. Nos. 8,067,609 and 8,138,348; and U.S. Patent Application Publications 2008/0058486, 2008/0188633, and 2008/0200743 all disclose the use of catalyst systems which are soluble in light paraffins, such as $C_3$ to $C_6$ iso- and normal-paraffins, and which exhibit high activities and improved selectivities at very moderate temperatures of 60° C. to 80° C. The use of such light solvents and mild reaction temperatures results in at least a portion, if not most or all, of the byproduct polymer being formed as an insoluble precipitate. Some of the insoluble polymer precipitates on the surfaces within the reactor and in the outlet piping. The insoluble polymer which does not stick to these surfaces exits the reactor as a suspended solid.

Prior art methods for dealing with the presence of active catalyst and byproduct polymer in the trimerization reactor effluent have problems. For example, the Cr-based trimerization catalysts typically employ an excess of aluminum alkyl activator relative to Cr compounds. In some systems, this excess can be 100:1 molar equivalents of Al to Cr or more, even up to 1000:1. The alcohols used to deactivate the catalyst are not selective to the Cr compounds since the alcohol also reacts with the Al compounds. An excess of alcohol over both Cr and Al is therefore required to ensure all active Cr species have reacted. The '451 and '612 patents discussed above, for example, teach use of a 5:1 molar excess of alcohol to total metals. If the Al:Cr ratio is 200:1 and a molar excess of alcohol to total metals of 5:1 is employed, then the molar excess of alcohol to Cr compound is 1000:1. This exceedingly high excess requirement for alcohol is costly, and also requires the addition of a distillation column for recovery of the unreacted alcohol for efficient utilization of the alcohol.

Prior art methods for separating byproduct polymer from the reactor effluent can also be cumbersome. Not all of the polymer contained in the reactor effluent can be separated by filtration, even if the effluent is cooled. Some of the polymer is still in solution, which carries through to the distillation columns. As the polymer is concentrated through successive distillation steps to recover reactants, products, and diluents, the polymer can precipitate and foul the column internals and reboilers.

Finally, build-up of byproduct polymer remaining within the oligomerization reactor and associated reactor piping can be troublesome. After byproduct polymers like polyethylene have fouled internal reactor surfaces and piping, it may become necessary to shut down the reactor(s) and wash the reactor(s) and piping out with a suitable solvent or wash liquid which can remove built up byproducts. Shutting down the reactor(s) for cleaning and maintenance is, of course, economically undesirable.

The byproduct polymer can be washed from the process using a hot solvent. In one embodiment of an ethylene trimerization process, as disclosed in WO 2011/112184, which is incorporated in full herein by reference, the byproduct polymer ends up as a dilute mixture with this solvent. A method to separate the byproduct polymer from this mixture and thus recover the solvent for recycle to the process, without fouling process equipment, is needed. This disclosure is directed to such a method.

SUMMARY

This disclosure relates generally to low temperature steam stripping methods for byproduct polymer and solvent separation and recovery from an ethylene oligomerization process. In an embodiment, this invention is directed to a method for separating byproduct polymer from the reactor effluent in an ethylene oligomerization process comprising:
  a. contacting the reactor effluent, comprising alpha-olefin product, byproduct polymer, catalyst material, and reactor diluent, with at least one heated solvent to make a heated reactor effluent;
  b. in a flash separator, separating the heated reactor effluent into a vapor stream comprising a portion of the alpha-olefin product and a liquid solvent effluent stream comprising a portion of the byproduct polymer;
  c. in a stripping vessel, removing at least a portion of the solvent from the solvent effluent stream by vaporizing the solvent at sub-atmospheric pressures and temperatures less than 90° C. to create a liquid stream rich in byproduct polymer;
  d. contacting the byproduct polymer rich stream with steam and water while controlling pressure and temperature conditions as in (c) to form a byproduct polymer water slurry; and
  e. discharging the byproduct polymer water slurry from the process.

The above method has surprisingly been found to separate byproduct polymer from the solvent without fouling process equipment or causing other process problems. The byproduct polymer ends up as flowable solid particles in a water stream that may be easily discharged from the process, while solvent is recovered for recycle to the process. In embodiments of the invention, over 90 wt % of the solvent used is recovered and the discharged byproduct polymer is less than 20 wt % solvent.

DESCRIPTION OF THE FIGURES

The invention will be described with reference to the following figures:
  FIG. 1: flow diagram for exemplary low temperature steam stripping process.

DETAILED DESCRIPTION

Specific embodiments of the invention are described herein. However, this is for exemplary purposes only and simply provides a context for further understanding the invention. The invention is not limited to the embodiments described below, but includes all alternatives, modifications, and equivalents that would be understood by one skilled in the art to fall within the spirit and scope of the appended claims.
Oligomerization Process This disclosure relates generally to low temperature steam stripping methods for byproduct polymer and solvent recovery from an ethylene oligomerization process. Catalytic trimerization of ethylene to selectively produce 1-hexene is a well-known process. Reactants, catalysts, diluents, reaction conditions, and process apparatus configurations are disclosed, for example, in U.S. Pat. Nos. 6,380,451 and 7,157,612 and in U.S. Patent Application Publications 2008/0058486, 2008/0182989, 2008/0188633, 2008/0200626, and 2008/0200743. These documents are incorporated herein by reference.

In the methods disclosed herein, the olefin feed may be ethylene. Ethylene may be oligomerized to form butene (dimerization), hexene (trimerization), octene, decene, and higher-order oligomers. The advantages of this method may also be extended to the dimerization, trimerization, etc., of other olefins, such as propylene, 1-butene, 2-butene, and the like, alone or as part of the reactor feed with ethylene.

Catalyst systems to promote the oligomerization will generally comprise homogeneous, organometallic systems such as single site chromium catalyst systems. Such systems can comprise a chromium source in combination with a heterocyclic, di-aryl, or phosphorus compound such as a pyrrole, pyridyl, or pyridyl-phosphino compound, along with an alkyl aluminum activator such as methyl alumoxane (MAO) or modified methyl alumoxane (MMAO). These and other suitable catalyst systems are well known in the industry.

The olefins) and/or catalyst system will generally be fed to the oligomerization reactor along with a suitable diluent. Diluents used herein will generally have a boiling point from about −20° C. to 120° C. Such a diluent can typically be an inert hydrocarbon, such as $C_3$ to $C_6$ normal and iso-paraffins, but can also be a cycloparaffin or aromatic compound. Olefins themselves can also be used as diluents, but are not preferred since they can also react depending on the catalyst system and conditions. Examples of diluents include 1-butene, 1-hexene, 1-octene, toluene, propane, butane, isobutane, pentane, isopentane, heptane, octane, nonane, decene, and combinations thereof. As used herein, the term "diluent" is distinct from the term "solvent" which, as hereinafter noted, is reserved for the material(s) used as the heat transfer media for conducting the flash vaporization of the reactants, products, and diluents.

The oligomerization reaction may involve any suitable reactor configuration, which may be selected by one skilled in the art based on factors such as olefin feedstock, catalyst system, and desired product. In an embodiment of the invention, the reactor system and process is adapted to include a liquid phase region and a vapor phase region, as described in WO 2011/112184, and such description is incorporated herein by reference. In this embodiment of the invention, the feed streams to the reactor enter the reactor in the liquid phase region, regardless of the state of the materials in the stream.

Oligomerization conditions such as temperature, pressure, flow rates, and residence times are conventional and well known. The reaction temperature may be maintained between about 25° C. and about 150° C., more preferably between about 50° C. and 90° C. The oligomerization reaction is exothermic. In an embodiment of the invention, conditions within the reactor may be controlled by evaporative cooling to maintain a desired temperature range. For example, evaporation of the liquid phase and evacuation of the resultant vapor phase, or portions thereof, may withdraw sufficient energy of vaporization from the reactor to maintain a desired temperature. In another embodiment of the invention, a desired temperature range may be maintained by introducing excess monomer to maintain a specific rate of evaporation. In other embodiments of the invention, the temperature and/or the pressure may be controlled by other means, such as through the use of cooling equipment or pressurization equipment, within the reactor and/or on one or more of the feed streams. Suitable cooling equipment may include, for example, a loop that circulates coolant through a cooling surface inside the reactor and back to a chiller outside the reactor.

The reaction pressure can generally be between about 0 psi (0 kPa) to 1200 psi (8273 kPa), more preferably from about 150 psi (1034 kPa) to about 900 psi (6206 kPa).

The catalyst reaction residence time can generally be about 30 minutes to about 6 hours. Alternatively, the induction period of the catalyst may be longer than 30 minutes and the reactor may be controlled to provide a catalyst reaction residence time of between about 60 minutes and about 6 hours.

Separation

After leaving the reactor system, the reactor effluent stream, comprising alpha-olefin product, byproduct polymer, catalyst material, reactor diluent, and unreacted olefin feed is contacted with at least one heated solvent. In an embodiment of the invention, the pressure of the effluent stream is reduced prior to this contacting. After this reduction, the pressure of the effluent stream should be from about 0 psig (0 kPa) to about 200 psig (1379 kPa), more preferably from about 50 psig (345 kPa) to about 150 psig (1034 kPa). Contact of the reduced pressure effluent stream with the at least one heated solvent is such as to rapidly heat the effluent stream in-situ. Prior to the contacting, the solvent(s) will generally be heated to a temperature above that of the effluent stream exiting the reactor and above the melting point of the byproduct polymer. Typically, the temperature of the solvent(s) just prior to the contacting with the reactor effluent will be from about 120° C. to 300° C., more preferably from about 130° C. to 200° C. The solvent(s) may be heated using a recirculating solvent heater or other suitable method.

While referred to herein as a "solvent," the primary function of this heated liquid is heat transfer. This "solvent" therefore need not actually dissolve anything or exhibit solvent-type properties. The most important characteristic of the solvent is to have a high enough boiling point that a major portion is maintained in the liquid phase in the flash separator, and such that any solvent vaporized in the flash separator is easy to separate from the alpha-olefin product by distillation. Useful solvents will generally have a boiling point from about 100° C. to about 220° C., and preferably at least 50° C. higher than the boiling point of the reaction diluent. In an embodiment of the invention, the solvent has a boiling point according to ASTM D1160 of 117° C. to 136° C. The solvent will generally also be inert. Exemplary solvents include $C_8$ and higher normal and iso-paraffins, $C_7$ and higher cycloparaffins, and $C_6$ and higher aromatics. In an embodiment of the invention, the solvent is an aliphatic compound.

High boiling olefinic byproducts ($C_8$ and heavier) of the reaction are also inevitably present in the reactor effluent and can be part of the solvent. In an embodiment of the invention, the entire solvent consists of material that was produced in the reaction step. Such byproducts, typically $C_8$, $C_{10}$, and $C_{12}$ linear and straight-chain molecules, are mostly olefinic in nature. Because of their olefinic nature, they are not truly inert, that is, they may undergo additional reactions in the presence of the un-passivated catalyst metals species. In another embodiment of the invention, at least a portion of the olefinic byproducts in the reactor effluent can be hydrogenated to saturate these olefins, forming iso- and normal-paraffins. These hydrogenated byproducts can then be recycled to serve as inert solvent for the flash separation.

In an embodiment of the invention, the solvent is specifically chosen to enhance the ability of the solvent and byproduct polymer to be separated. Since, as noted above, the primary purpose of the solvent is heat transfer, and not necessarily to dissolve polymer, selection of a fluid in which polymer does not readily dissolve can be useful in some embodiments of the invention. Examples of such solvents are $C_8$ to $C_{12}$ iso- and normal-paraffins and olefins. Lighter boiling solvents are not preferred because they are difficult to separate from a typical product, such as hexene. Heavier solvents are not preferred because they are difficult to remove from the byproduct polymer.

After contacting with the solvent, the heated reactor effluent stream is then sent to a flash separator. The pressure of the heated reactor effluent stream, and the pressure in the flash separator, should be from about 0 psig (0 kPa) to about 200 psig (1379 kPa), more preferably from about 50 psig (345 kPa) to about 150 psig (1034 kPa). The temperature of the heated reactor effluent stream, and the initial temperature in the flash separator, will generally be about 100° C. to about 200° C. The steady state temperature in the flash separator will depend on the boiling point of the solution in the flash separator at the operating pressure. Higher operating pressures require higher steady state temperatures. As the solvent will generally be a heavier component in the stream, the use of heavier solvents or an increased amount of solvent will also increase the boiling temperature of the solution and therefore increase the steady state operating temperature of the flash separator. Heat flow into the flash separator should be sufficient to vaporize the majority of alpha-olefin product and unreacted olefin feed and avoid accumulation of material. This heat flow can be controlled independent of the temperature in the flash separator by, for example, adjusting the flow rate of an external heating loop or the return temperature from an external heating loop.

The result of the flash step is separation of the heated reactor effluent stream into 1) a vapor stream comprising a portion of the alpha-olefin product and optionally unreacted olefin feed and minor portions of the other olefin byproducts and solvent; and 2) a liquid solvent effluent stream comprising a portion of the byproduct polymer, solvent, and catalyst components and optionally a minor portion of alpha-olefin product or other olefin byproducts. If a light-boiling diluent is used in the reaction (such as $C_3$ to $C_6$ normal- or iso-paraffin or olefin), a major portion of this diluent will vaporize. In an embodiment of the invention, the vapor stream comprises a major portion of the alpha-olefin product and the liquid solvent effluent stream comprises a major portion of the byproduct polymer and/or a major portion of the solvent.

As used herein, "major portion" means at least about 50 wt %, based on the weight of that individual component in the solvent effluent stream prior to separation. In an alternative embodiment of the invention, the vapor stream may comprise at least about 60 wt %, 75 wt %, 85 wt %, or 95 wt % of the alpha-olefin product and the liquid stream may comprise at least about 60 wt %, 75 wt %, 85 wt %, or 95 wt % of the byproduct polymer, solvent, or catalyst components, based on the weight of that individual component in the solvent effluent stream prior to separation. As used herein, "minor portion" means less than about 50 wt %, based on the weight of that individual component in the solvent effluent stream prior to separation.

The method described herein thus addresses the problem of the presence of active catalyst and byproduct polymer in the reactor effluent in a single process step. An interesting feature of this method is that the catalyst in the reactor effluent is not necessarily "killed" by the flash separation step. Instead, the reactive species are quickly separated from the catalyst, such that the catalyst has no reactants to catalyze. This avoids the need to add excess amounts of an external kill agent, such as alcohol, and the need to recover and recycle the kill agent in the downstream distillation process.

The vapor stream from the flash separator may be fed to one or more distillation columns for recovery of alpha-olefin product, unreacted olefin feed, other olefin byproducts, solvent, and diluent. Byproduct polymer and catalyst components in the solvent effluent stream introduced into the flash separator are not volatile and generally absent from the vapor stream.

The liquid solvent effluent stream from the flash separator, comprising a dilute byproduct polymer/solvent mixture, is processed further to separate the byproduct polymer from the solvent, such that byproduct polymer may be discharged from the process and solvent may be recycled. In an embodiment of the invention, this liquid solvent effluent stream may optionally be sent to an initial stripping vessel, where temperatures above 120° C. and pressures above atmospheric are applied to vaporize solvent until the composition of the remaining liquid stream is concentrated to from about 1 wt % to about 10 wt % byproduct polymer, based on the total weight of the stream.

Following this optional initial stripping step, the liquid solvent effluent stream, comprising the concentrated byproduct/solvent mixture (or dilute byproduct/solvent mixture, if the initial stripping step is not applied), is processed further. These steps will be described with reference to FIG. 1. Without cooling, this liquid solvent effluent stream S19 is released to a stripping vessel D-12 under vacuum pressure to adiabatically flash as much solvent as possible from the mixture. The vacuum may be attained by vacuum pump, ejector system, or other suitable method, and is controlled to attain a temperature of the mixture of less than 90° C., preferably between about 50° C. to about 90° C. In addition to vaporizing solvent, this flash causes some of the byproduct polymer to begin to solidify and crystallize. In an embodiment of the invention, the overall method disclosed herein allows over 90 wt % of the solvent in the process to be recovered, based on the total weight of solvent used. In an embodiment of the invention, at least about 30% of this solvent recovery occurs in this flash step.

The result of this stripping step is a liquid stream rich in byproduct polymer. The term "rich" in this disclosure simply means that a higher concentration of byproduct polymer is achieved in the liquid stream in this step than what is achieved in any prior step. Next, steam S40, water, and optionally an inert gas (such as nitrogen S34), are introduced into the vessel to strip additional solvent from this byproduct polymer rich stream. This may be done with or without agitation. In an embodiment of the invention, such as is shown in FIG. 1, the vessel comprises an agitator that is a mechanical mixer. Other known methods of agitation are suitable. The inert gas flow, steam flow, and vessel pressure are adjusted as needed to keep the temperature of the slurry below about 90° C. Sufficient water level is maintained such that, as the last of the solvent vaporizes, the byproduct polymer is left as flowable solid particles in the water. By maintaining the temperature as described, the byproduct polymer attains enough crystallinity as the solvent vaporizes that it is non-sticky and does not cause fouling or other processing problems.

During vacuum operation in the stripping vessel D-12, the vapors are condensed and sent to a separator vessel D-13, where the solvent and water are decanted. With the proper choice of solvent boiling points, as described above, a majority of the solvent and water condenses, minimizing the load on the vacuum compressor S42. The solvent phase S43 may be further distilled and recycled to the process, while the water phase can be recycled to the stripping vessel D-12, heated to produce steam for stripping, purged to waste disposal, or any combination of these.

After the desired level of solvent is stripped from the byproduct polymer, the vacuum is removed and the water/polymer slurry is discharged from the stripping vessel. Most of the water from this slurry can be removed with a strainer and sent to waste water S39, recycled to the process, or otherwise used. The wet, substantially solvent-free byproduct polymer mixture S38 can be discharged from the vessel, either batch-wise, continuously, or periodically. By "substantially solvent-free" it is meant that the discharged byproduct polymer is less than 20 wt % solvent, based on the total weight of the discharged byproduct polymer.

Additional steps may be employed to ensure that the byproduct polymer precipitates as small particles, and does not form large agglomerates that may be difficult to remove from the stripping vessel. In an embodiment of the invention, the byproduct polymer/solvent mixture may be added to the stripping vessel slowly such that small "crumbs" of polymer are formed, as these are easier to remove in a continuous or periodic fashion. The addition of this stream too quickly can, in some embodiments of the invention, cause large "chunks" of polymer to form, which are more difficult to remove from the vessel.

In other embodiments of the invention, the byproduct polymer/solvent mixture may be injected into the stripping vessel under conditions of high shear. The high shear can be achieved by a high velocity nozzle, high velocity steam co-injection, mechanical agitation, or any combination thereof. In other embodiments of the invention, surface-active material may be added to the stripping vessel to reduce the tendency of the polymer particles to stick together.

In some embodiments of the invention, solvents such as ISOPAR G™ or ISOPAR H™, available from ExxonMobil Chemical Company with a business office in Houston, Tex., may be used. Such solvents result in a cloudy appearance of the liquid phase generated in the flash separation. This means that at least some of the polymer is not in solution, but rather in a fluid suspension within the solvent. Upon cooling of a polymer-containing "solvent" stream, additional polymer precipitates. Upon settling, the "polymer-rich" phase settles to the bottom, and a clear liquid layer appears on top. Such settling can be used to concentrate byproduct polymer in the liquid before stripping, reducing the amount of solvent that must be stripped. Further increasing the concentration of byproduct polymer in this way before stripping reduces the amount of time and steam required to remove solvent from the byproduct polymer. When a settling step is used, the upper liquid layer ("polymer-lean" liquid) can be recycled to the flash separator. While the upper liquid layer will not be free of dissolved polymer or catalyst components, one skilled in the art will recognize that the system can be operated at a steady state, such that the rate of purging of byproduct polymer in the polymer-rich phase will equal the production rate.

The vapor stream leaving the stripping vessel mainly comprises water and solvent vapors. Upon cooling, the water and solvent can be condensed at temperatures above ambient. Most of the water is easily separated from the solvent by settling and decanting. The solvent layer, however, will still be saturated with dissolved water. It is important to remove this water before recycling the solvent to the flash separation. If wet solvent were recycled, some of the water would flash and recycle to the reactor with the ethylene and/or reaction diluent. One method of removing water from the recycle solvent is to pass the water-containing solvent over a bed of desiccant. In an embodiment of the invention, this requires at least one additional vessel for the desiccant, plus either a regeneration system or periodic replacement of the desiccant with fresh material. In another embodiment of the invention, the recycle solvent can be dried by distillation, utilizing a column already present in the process such that no additional vessels, desiccant replacement, or regeneration systems are required. In an embodiment of the invention, at least 90 wt %, at least 95 wt %, or at least 99 wt % of solvent is recovered, based on the total weight of solvent used.

EXAMPLES

The following operating example provides a context for further understanding the invention. The invention is not limited to the method or any of the embodiments described below, but includes all alternatives, modifications, and equivalents that would be understood by one skilled in the art to fall within the spirit and scope of the appended claims.

In this disclosure, density was measured according to ASTM D1505.

Example 1

The following process was followed for Example 1. Where the details of a process step are not specifically included, the general processes as outlined above were followed.

The reactor effluent stream from an ethylene oligomerization was contacted with a heated solvent and sent through a flash separator to separate the stream into vapor and liquid streams. The liquid stream, comprising the byproduct polymer/solvent mixture, was fed into a stripping vessel comprising a mechanical agitator, with the agitator initially off. Steam and water flows were also initially off. The low pressure in the stripping vessel caused a significant amount of solvent to flash while the byproduct polymer remained in the liquid phase, with no added heat. The mixture was then allowed to cool below the sticking temperature of the byproduct polymer. "Sticking temperature," for purposes of this example and disclosure, is the temperature at which the polymer is sticky, in other words, warm enough to coat surfaces of the reactor and associated piping. This temperature could be readily determined by one skilled in the art in possession of this disclosure.

After cooling, the agitator in the stripping vessel was started at high enough revolutions per minute ("rpm") to produce vigorous mixing of the remaining liquid byproduct polymer/solvent mixture. Steam was allowed to flow into the vessel, but the pressure was maintained low enough that the boiling point of the steam was below the sticking temperature of the byproduct polymer. To recover the byproduct polymer, all flows were stopped and the vessel was re-pressurized. Condensate was purged from the vessel with the recovered byproduct polymer particles. The water and condensate were separated using a simple filter.

Results of Example 1 are summarized in Tables 1 and 2 below, which can also be better understood by reference to the process diagram in FIG. 1. Table 1 summarizes properties for several streams shown in FIG. 1, as well as S43A, the vapor stream exiting the flash separator after the initial flash, and S43B, the final liquid stream exiting the flash separator demonstrating total recovery of byproduct polymer in the process. The results below demonstrate that over 99 wt % of the solvent is recovered in this process. About 30% of this recovery occurs during the initial adiabatic flash.

TABLE 1

Stream Properties from Example 1

| Stream Name | S19 (polymer/ solvent mixture) | S34 (nitrogen) | S38 (by- product polymer) | S39 (waste water) | S40 (steam) | S43A (initial flash) | S43B (total recovery) |
|---|---|---|---|---|---|---|---|
| Temperature, °C. | 197.7 | 25.0 | 38.3 | 38.3 | 185.5 | 31.7 | 25.0 |
| Pressure, psia | 70.0 | 150.0 | 1.0 | 1.0 | 165.0 | 1.0 | 1.0 |
| Liquid wt % Fraction | 1 | 0 | 1 | 1 | 0 | 0 | 1 |
| Total Molar Rate, kg-mol/hr | 18 | 0 | 0 | 555 | 555 | 16 | 18 |
| Total Mass Rate, kg/hr | 2253 | 0 | 46 | 10,000 | 10,000 | 798 | 2207 |
| Density, kg/m$^3$ | 542 | 12 | 781 | 991 | 6 | 0 | 703 |

TABLE 2

Weight Compositions of Streams from Example 1, kg/hr

| Stream Name | S19 (polymer/ solvent mixture) | S34 (nitrogen) | S38 (by- product polymer) | S39 (waste water) | S40 (steam) | S43A (initial flash) | S43B (total recovery) |
|---|---|---|---|---|---|---|---|
| Nitrogen | 0.00 | 0.00 | 0.00 | 0.00 | 0.00 | 0.00 | 0.00 |
| Ethene | 0.00 | 0.00 | 0.00 | 0.00 | 0.00 | 0.00 | 0.00 |
| 2-Methyl-butane | 0.45 | 0.00 | 0.00 | 0.00 | 0.00 | 0.43 | 0.45 |
| 1-Hexene | 14.22 | 0.00 | 0.00 | 0.00 | 0.00 | 12.06 | 14.22 |
| 2-Methyl-heptane | 537.36 | 0.00 | 0.11 | 0.00 | 0.00 | 216.00 | 537.25 |

TABLE 2-continued

Weight Compositions of Streams from Example 1, kg/hr

| Stream Name | S19 (polymer/ solvent mixture) | S34 (nitrogen) | S38 (by- product polymer) | S39 (waste water) | S40 (steam) | S43A (initial flash) | S43B (total recovery) |
|---|---|---|---|---|---|---|---|
| 2,6-Dimethyl-heptane | 1601.85 | 0.00 | 0.87 | 0.00 | 0.00 | 377.35 | 1600.97 |
| 1-Decene | 54.05 | 0.00 | 0.17 | 0.00 | 0.00 | 3.06 | 53.88 |
| 1-Eicosene[1] | 45.06 | 0.00 | 44.17 | 0.00 | 0.00 | 0.00 | 0.35 |
| $H_2O$ | 0.00 | 0.00 | 0.01 | 9999.85 | 10000.0 | 189.57 | 0.21 |

[1] "1-Eicosene" is a surrogate name for the byproduct polymer. In reality, this product comprises one or more heavy polymers which do not vaporize out of solution under these conditions.

The invention claimed is:

1. A method for separating byproduct polymer from the reactor effluent in an ethylene oligomerization process comprising:
   a. contacting said reactor effluent, comprising alpha-olefin product, byproduct polymer, catalyst material, and reactor diluent, with at least one heated solvent to make a heated reactor effluent;
   b. in a flash separator, separating said heated reactor effluent into a vapor stream comprising a portion of said alpha-olefin product and a liquid solvent effluent stream comprising a portion of said byproduct polymer;
   c. in a stripping vessel, removing at least a portion of said solvent from said solvent effluent stream by vaporizing said solvent at sub-atmospheric pressures and temperatures less than 90° C. to create a liquid stream rich in byproduct polymer;
   d. contacting said byproduct polymer rich stream with steam and water while controlling pressure and temperature conditions as in (c) to form a byproduct polymer water slurry; and
   e. discharging said byproduct polymer water slurry from said process.

2. The method of claim 1, wherein said contacting in (a) occurs at pressures of 0 psig (0 kPa) to about 200 psig (1379 kPa) and temperatures of about 100° C. to about 200° C.

3. The method of claim 1, wherein said temperatures in (c) are between 50° C. and 90° C.

4. The method of claim 1, further comprising, prior to (c):
   in an initial stripping vessel, applying temperatures above 120° C. and pressures above atmospheric to said liquid solvent effluent stream in (b) to vaporize solvent until the composition of said stream is from 1 wt % to 10 wt % byproduct polymer, based on the total weight of said stream.

5. The method of claim 4, wherein said temperatures are about 150° C. or higher and said pressures are about 80 psig (552 kPa).

6. The method of claim 1, further comprising, prior to (b): reducing the pressure of said heated reactor effluent to from about 0 psig (0 kPa) to about 200 psig (1379 kPa).

7. The method of claim 1, wherein said stripping vessel comprises an agitator.

8. The method of claim 7, wherein said agitator is a mechanical mixer.

9. The method of claim 1, wherein said stripping vessel does not comprise an agitator.

10. The method of claim 1, wherein said byproduct polymer rich stream is further contacted with an inert gas in (d).

11. The method of claim 10, wherein said inert gas is nitrogen.

12. The method of claim 1, wherein said solvent is an aliphatic compound.

13. The method of claim 1, wherein said solvent has a boiling point according to ASTM D1160 of 100° C. to 220° C.

14. The method of claim 1, wherein said solvent is heated to a temperature of 120° C. to 300° C. prior to said contacting in (a).

15. The method of claim 1, wherein over 90 wt % of said solvent from (a) is recovered in the method, based on the total weight of solvent used.

16. The method of claim 15, wherein at least about 30% of said solvent recovery occurs in (c) of claim 1.

17. The method of claim 1, wherein recovered solvent is recycled back to the process.

18. The method of claim 1, wherein said discharged byproduct polymer is less than 20 wt % solvent, based on the total weight of said discharged byproduct polymer.

19. The method of claim 1, wherein water is separated from said byproduct polymer water slurry prior to said discharging and said water is recycled to the process.

20. The method of claim 1 wherein said vapor stream in (b) comprises a major portion of said alpha-olefin product and said liquid solvent effluent stream in (b) comprises a major portion of said byproduct polymer.

21. The method of claim 1 further comprising:
   a. subjecting said vapor phase in (a) to one or more distillation steps to separate and recover or recycle alpha-olefin product, unreacted ethylene, or reactor diluent.

* * * * *